US00PP19397P2

(12) United States Plant Patent
Carruth

(10) Patent No.: US PP19,397 P2
(45) Date of Patent: Oct. 28, 2008

(54) SHRUB ROSE PLANT NAMED 'WEKCLAFLOBO'

(50) Latin Name: *Rosa hybrida*
Varietal Denomination: WEKclaflobo

(75) Inventor: Thomas F. Carruth, Altadena, CA (US)

(73) Assignee: Weeks Wholesale Rose Grower, Inc., Rancho Cucamonga, CA (US)

( * ) Notice: Subject to any disclaimer, the term of this patent is extended or adjusted under 35 U.S.C. 154(b) by 0 days.

(21) Appl. No.: 11/985,089

(22) Filed: Nov. 13, 2007

(51) Int. Cl.
*A01H 5/00* (2006.01)

(52) U.S. Cl. ..... Plt./104

(58) Field of Classification Search ..... Plt./104, Plt./107

See application file for complete search history.

*Primary Examiner*—Annette H Para
*Assistant Examiner*—S. B. McCormick-Ewoldt
(74) *Attorney, Agent, or Firm*—Christie, Parker & Hale LLP

(57) ABSTRACT

A new variety of Shrub rose suitable for garden decoration, having flowers of ever-changing yellows and blushing pinks coloration.

1 Drawing Sheet

Classification: The present invention relates to a new *Rosa hybrida* plant.

Variety denomination: The new plant has the varietal denomination 'WEKclaflobo'.

BACKGROUND OF THE INVENTION

This invention relates to a new and distinct variety of Shrub Rose. It has an undisseminated seedling of my creation as its seed parent with the following genetic origin Santa Claus×Flower Carpet and as its pollen parent the variety known as 'WEKplapic' (U.S. Plant Pat. No. 11,517).

SUMMARY OF THE INVENTION

Among the features which distinguish the new variety from other presently available and commercial rose cultivars known to the inventor are the following combination of characteristics: its very long foliaceous appendages on the surface of the bud, its ever-changing yellows and blushing pinks coloration, its red suffusion on the inner surface of the sepal that appears as the flower ages and its red suffusion on the under side of the mature leaf. The plant has a bushy moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKclaflobo' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, an undisseminated seedling of my creation by the following combination of characteristics: whereas 'WEKclaflobo' bears medium sized flowers (about 6.5 to about 9.3 cm. in diameter) of ever-changing yellows and blushing pinks coloration, the undisseminated seedling bears significantly smaller flowers of yellow coloration. The new variety is classified as a shrub rose with a bushy moderately spreading medium height growing habit, whereas the seed parent is classified as a floribunda rose with a significantly smaller and rounded growing habit.

The new variety may be distinguished from its pollen parent, 'WEKplapic' by the following combination of characteristics: whereas 'WEKclaflobo' bears single flowers (about 5 to 6 petals) of every-changing yellows and blushing pinks coloration, 'WEKplapic' bears semi-double flowers with significantly heavier petalage (about 9 to 12 petals) of ivory edged red coloration. The new variety is classified as a shrub rose with a bushy moderately spreading medium height growing habit (about 60 to about 80 cm. spread at the widest point), whereas the pollen parent is classified as a floribunda rose with a upright medium height significantly more spreading growing habit (about 105 to about 130 cm. spread at the widest point).

COMPARISON WITH THE CLOSEST COMMERCIALLY AVAILABLE CULTIVAR

The closest commercially available cultivar to the new variety is the pollen parent 'WEKplapic'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety sometimes bears its flowers singly, usually in clusters of three to six or more per stem. Flowers may be borne in regular rounded clusters on strong somewhat short stems (about 10 to about 38 cm). Outdoors, the plant blooms abundantly and nearly continuously during the growing season. The flowers have a moderate fruity to apple-like fragrance.

BUD

The peduncle is about 1.9 to about 3.5 cm. in length, of slender caliper (about 0.15 to about 0.2 cm. in diameter), and usually erect. It is somewhat rough, with some stipitate glands. Peduncle color is between 144A and 146B often moderately suffused, especially on the side exposed to the sun, with between 183A and 187B.

Before the calyx breaks, the bud is about 0.9 to about 1.5 cm. in diameter at the widest point, about 1.5 to about 2.1 cm. in length, and pointed in shape with a somewhat conspicuous neck. The surface of the bud bears few very long foliaceous appendages and some stipitate glands, usually with slender entire foliaceous parts extending beyond the tip of the bud about ¾ or more of its length. Bud color is between 146B and 144A often heavily suffused, especially on the side exposed to the sun, with between 183A and 187A.

The sepals are about 2.4 to about 3.2 cm. in length and about 0.6 to about 1.1 cm. in width at the widest point. The outer surface color of the sepal is between 146B and 144A often heavily suffused, especially on the side exposed to the sun, with between 183A and 187B. The inner surface color of the sepal is between 137B and 144B. After the sepals open, the inner surface color is often heavily suffused, especially on the area exposed to the sun, with between 187A and 187B. The sepals are covered with fine wooly tomentum; sepal margins are lined with some stipitate glands and few hairs.

The receptacle of the flower is of medium length (about 0.5 to about 0.7 cm.) and average in caliper (about 0.5 to about 0.6 cm. in diameter). The receptacle is globular to moderately rounded in form. Its surface is smooth with thick fleshy walls. The receptacle color is between 146B and 144A often heavily suffused, especially on the side exposed to the sun, with between 183A and 187B.

As the petals open (after the calyx breaks), the bud is about 1.3 to about 2.1 cm. in diameter at the widest point, about 2.0 to about 2.6 cm. in length, and moderately ovoid to pointed in form. On the under surfaces of the newly opened petals, the color at the base of the petal is between 6C and 7C that gradually suffuses toward the center of the petal to between 18A and 20C, usually heavily blushed with between 53B and 53C to sometime as dark as between 187A and 187B. There is no visible change in coloration at the point where the petal attaches. On the upper surfaces of the newly opened petals, the color at the base of the petal is between 9B and 7A that gradually suffuses toward the center of the petal to between 19A and 20A, usually heavily blushed toward the petal edge with between 46A and 53B to sometime as dark as between 187A and 187B. There is no visible change in coloration at the point where the petal attaches.

BLOOM

When fully open, the bloom ranges from about 6.5 to about 9.3 cm. in diameter. Petalage is single with about 5 to 6 petals and about zero to one petaloid irregularly arranged. When partially open, the bloom form is moderately cupped to somewhat ovoid, and the petals are loosely spiraled to cupped with petal edges somewhat reflexed outward. When fully open, the bloom form is more flat to somewhat cupped, and the petals are loosely cupped with petal edges somewhat reflexed outward.

PETALS

The substances of the petals is moderately heavy and of medium to somewhat thick thickness, with upper surfaces somewhat satiny to slightly shiny and under surfaces slightly shiny to matte. The petals are about 3.2 to about 4.5 cm. in length and about 2.9 to about 4.1 cm. in width at the widest point. Petal margins are entire. The petals are moderately obovate in shape with rounded to sometimes mucronate apices.

Petaloids are about 1.9 to about 2.7 cm. in length and about 0.8 to about 1.0 cm. in width at the widest point. Petaloids are irregularly shaped somewhat subulate to oblanceolate with rounded apices.

NEWLY OPENED FLOWER

On the under surfaces of the newly opened petals, the color at the base of the petal is between 3D and 2C that gradually suffuses toward the center of the petal to between 18B and 19B, usually heavily blushed with between 53C and 52A to sometime as dark as between 187A and 187B. There is no visible change in coloration at the point where the petal attaches. On the upper surfaces of the new opened petals, the color at the base of the petal is between 6C and 15D that gradually suffuses toward the center of the petal to between 15D and 20D, usually heavily blushed toward the petal edge with between 53C and 52A to sometime as dark as between 187A and 187B. There is no visible change in coloration at the point where the petal attaches.

The under and upper surface color of the petaloids are similar in coloration to the upper and under surfaces of the petals.

The general tonality of the newly opened flower is between 6C and 15D at the base of the petal that gradually suffuses toward the center of the petal to between 15D and 20D, usually heavily blushed toward the petal edge with between 53C and 52A to sometime as dark as between 187A and 187B.

THREE-DAY-OLD FLOWER

The upper surface color of the petals is between 155C and 155D usually heavily blushed on the entire petal surface with between 61C and 58C to sometimes as dark as between 60B and 60A. The under surface color of the petals in similar to the upper surface color except that the blushed coloration does not cover the entire surface. There is no visible change in coloration at the point where the petal attaches on the upper and under surface.

The under and upper surface color of the petaloids are similar in coloration to the upper and under surfaces of the petals.

The general tonality of the three-day-old flower is between 155C and 155D usually heavily blushed on the entire petal surface with between 61C and 58C to sometime as dark as between 60B and 60A.

On the spent bloom, the petals usually drop off cleanly.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 95) and are arranged regularly about the pistils; a few are mixed with petaloids. The filaments are of medium length (about 0.6 to about 1.2 cm.) most with anthers. Filaments are near 13B in color sometimes lightly suffused with near 53C. The anthers are moderately small for the class and all open approximately at the same time. Anther color when immature is near 22A on the external part and near 20C on the internal part. Anther color at maturity is near 161B on the external part and near 200A on the internal part. Pollen is abundant and near 20B in color.

FEMALE REPRODUCTIVE ORGANS

Pistils vary in number (average about 35). The styles are moderately even, somewhat short in length (about 0.4 to about 0.6 cm.), average in caliper, and loosely bunched to somewhat separated. Stigma color is between 10A and 9C. Style color is between 4D and 2D often moderately suffused with between 53B and 53C. Ovaries are usually all enclosed in the calyx.

Hips are of average length (about 1.1 to about 1.6 cm.), rounded to moderately globular in form, and between 28A and 31A in color when ripe. The hip surface is very smooth with thick fleshy walls. The sepals are permanent, and usually straight in shape.

The seeds are irregularly rounded, smooth in texture, approximately 16 to about 20 per hip, about 0.5 to about 0.7 cm. in diameter at the widest point and between 164B and 165C in color.

FOLIAGE

The compound leaves are usually comprised of three to seven leaflet and are borne abundantly. The five-leaflet leaves are about 7.6 to about 12.4 cm. in length and about 6.4 to about 9.9 cm. in width at the widest point, moderately heavy it crisp in texture, and semi-glossy in finish. The terminal leaflets are about 3.4 to about 6.3 cm. in length and about 1.9 to about 4.3 cm. in width at the widest point, shaped ovate to somewhat oval with moderately acute apices and rounded bases. Their margins are usually simply serrate.

The upper surface color of the mature leaf is between 147A and 146A. The under surface color of the mature leaf is between 138A and 146B sometimes moderately suffused with between 187B and 183A. The upper surface color of the young leaf is between 147A and 146A, usually heavily suffused with between 187A and 183A. The under surface color of the young leaf is between 138A and 146B, usually heavily suffused with between 187B and 183A.

The rachis is average in caliper and rough. The upper side is shallowly grooved with some stipitate glands on the edges of the grooves. The under side of the rachis is rough with some stipitate glands and few small prickles. The rachis color is near 146D on the under side and near 146A on the upper side.

The stipules are about 0.6 to about 1.2 cm. in length and of medium width (about 0.4 to about 0.7 cm.) with somewhat short straight points that usually turn out at an angle of more than 45 degrees and sometimes recurve toward the stem. The stipules color is between 146D and 137A.

The petiole is average in caliper and rough. The upper side is shallowly grooved with some stipitate glands on the edges of the grooves. The under side of the petiole is rough with some stipitate glands and few small prickles. The petiole is about 1.2 to about 1.5 cm. in length and about 0.1 to about 0.2 cm in diameter at the widest point. The petiole color is near 146D on the under side and near 146A on the upper side.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has a bushy moderately spreading medium height growing habit (about 100 to about 120 cm. in height and about 60 to about 80 cm. spread at the widest point), with full branching. It displays moderately vigorous growth and the canes are of medium to somewhat light caliper for the class.

The color of the major stems is between 147B and 152A. They bear some large prickles that are about 0.6 to about 0.9 cm. in length. The large prickles are angled moderately downward with a medium length narrow oval base; prickle color is between 177B and 166B. The major stem bears few small prickles of similar shape and coloration.

The color of the branches is between 146B and 146A. They bear some large prickles which are of similar size and shape of the large prickles on the major stems; prickle color is between 164C and 164B. The branches bear some small prickles of similar shape and coloration.

The color of the new shoots is between 146B and 146A often moderately suffused with between 183B and 187B. They bear some medium size prickles which are of similar shape to the large prickles on the major stems. The medium size prickles are about 0.3 to about 0.5 cm. in length. Prickle color is between 153A and 151A usually heavily suffused with between 187B and 187C. The shoots bear some small prickles of similar shape and coloration.

I claim:

1. A new and distinct Shrub rose plant of the variety substantially as described and illustrated herein.

* * * * *

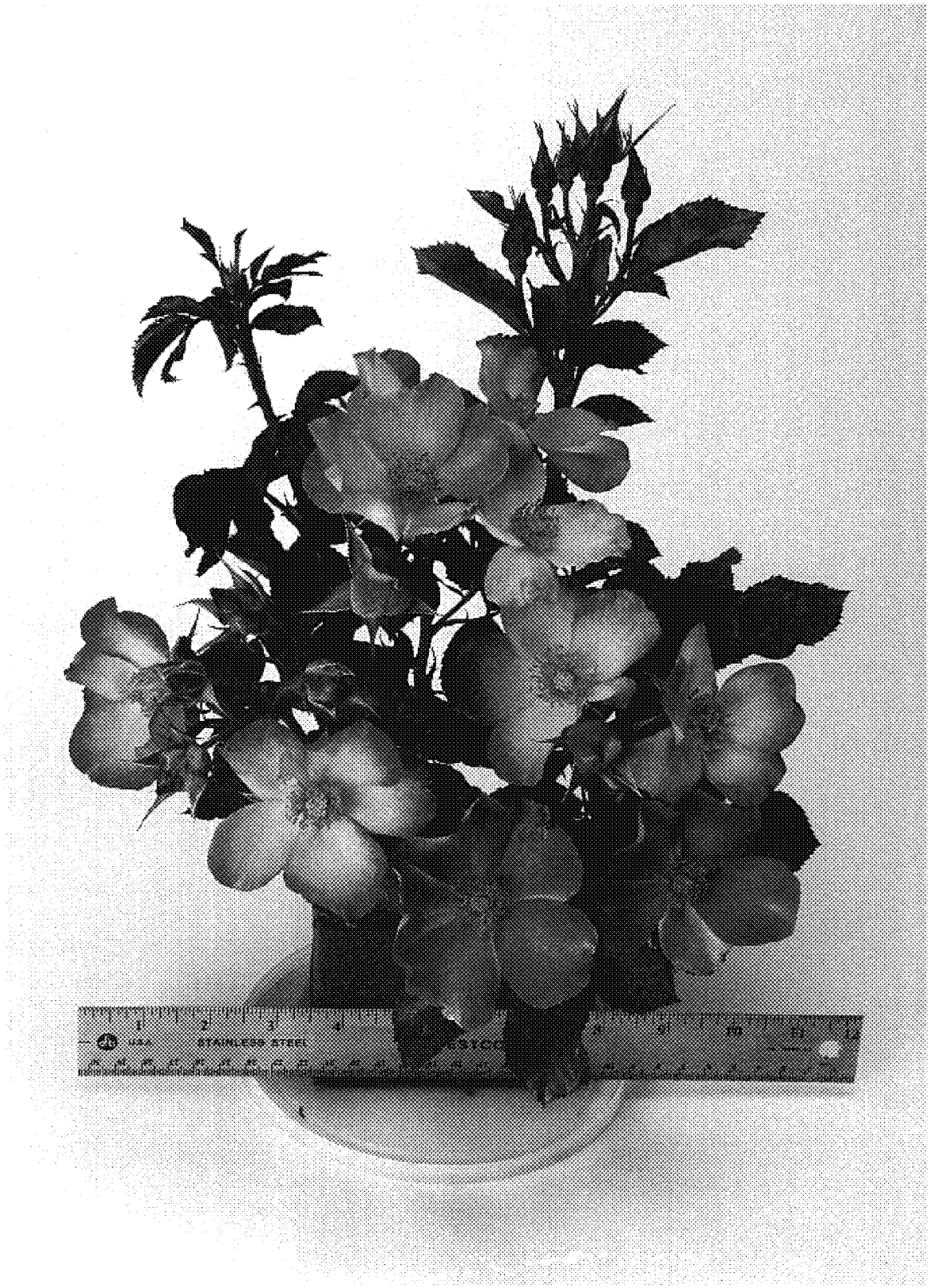
STAINLESS STEEL